United States Patent [19]

Hall

[11] Patent Number: 4,959,383

[45] Date of Patent: Sep. 25, 1990

[54] PHENYLSULFONE ALKENOIC ACIDS, DERIVATIVES THEREOF, COMPOSITIONS CONTAINING SAME AND METHOD OF USE

[75] Inventor: Steven E. Hall, Trenton, N.J.

[73] Assignee: E. R. Squibb & Sons, Inc., Princeton, N.J.

[21] Appl. No.: 264,938

[22] Filed: Oct. 31, 1988

[51] Int. Cl.$^5$ .................. A61K 31/41; A61K 31/21; A61K 31/19; A61K 31/18
[52] U.S. Cl. .................... 514/381; 514/510; 514/559; 514/568; 514/596; 514/532; 514/602; 514/605; 562/427; 562/429; 560/10; 560/11; 548/252; 564/92; 564/99
[58] Field of Search .............. 562/429, 427; 560/11, 560/10; 548/252; 514/510, 559, 568, 596, 532, 602, 605, 381; 564/92, 99

[56] References Cited

U.S. PATENT DOCUMENTS

| | | |
|---|---|---|
| 3,980,695 | 9/1976 | Chabardés et al. .............. 560/11 |
| 4,258,058 | 3/1981 | Witte et al. .............. 424/309 |
| 4,443,477 | 4/1984 | Witte et al. .............. 424/319 |
| 4,711,903 | 12/1987 | Mueller et al. .............. 548/252 |
| 4,752,613 | 6/1988 | Floyd et al. .............. 514/438 |
| 4,752,616 | 6/1988 | Hall et al. .............. 514/510 |

FOREIGN PATENT DOCUMENTS

| | | |
|---|---|---|
| 748454 | 12/1966 | Canada .............. 562/429 |
| 56172A2 | 7/1982 | European Pat. Off. . |
| 242518A1 | 2/1987 | European Pat. Off. . |
| 223593 | 5/1987 | European Pat. Off. . |
| 253257A2 | 7/1987 | European Pat. Off. . |
| 235575 | 9/1987 | European Pat. Off. .............. 562/429 |
| 261539A2 | 9/1987 | European Pat. Off. . |
| 3629929A1 | of 0000 | Fed. Rep. of Germany . |
| 3622865A1 | 1/1988 | Fed. Rep. of Germany . |

*Primary Examiner*—Frederick E. Waddell
*Attorney, Agent, or Firm*—Burton Rodney

[57] ABSTRACT

Phenylsulfone alkenoic acids and derivatives thereof are provided which have the structure

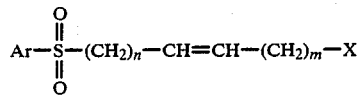

wherein Ar represents an aryl group including phenyl or naphthyl which may or may not include one or more substituents, X is COOR wherein R is hydrogen, alkali metal or lower alkyl or X is 5-tetrazolyl or

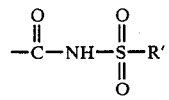

wherein R' is lower alkyl or aryl; n is 2, 3 or 4 and m is 2, 3 or 4. These compounds are cardiovascular agents which exhibit thromboxane antagonist activity and thus are useful in the treatment of thrombotic and vasospastic disease.

9 Claims, No Drawings

PHENYLSULFONE ALKENOIC ACIDS, DERIVATIVES THEREOF, COMPOSITIONS CONTAINING SAME AND METHOD OF USE

FIELD OF THE INVENTION

The present invention relates to phenylsulfone alkenoic acids and derivatives thereof which are useful in the treatment of thrombotic disease and vasospastic disease.

BACKGROUND OF THE INVENTION

U.S. Pat. No. 4,258,058 discloses phenoxyalkyl carboxylic acids which inhibit thrombocyte aggregation and depress serum lipids and have the structure

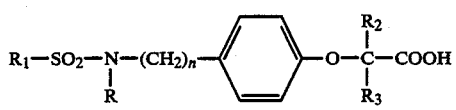

wherein R is hydrogen or lower alkyl;
$R_1$ is an alkyl or aryl, aralkyl or aralkenyl radical, the aryl moiety of which can be substituted one or more times by halogen, hydroxyl, trifluoromethyl or lower alkyl, alkoxy or acyl;
$R_2$ and $R_3$, which can be the same or different, are hydrogen or lower alkyl and
n is 0, 1, 2 or 3;
as well as the physiologically acceptable salts, esters and amides thereof.

U.S. Pat. No. 4,443,477 discloses sulphonamidophenyl carboxylic acids which inhibit thrombocyte aggregation and depress serum lipids and have the structure

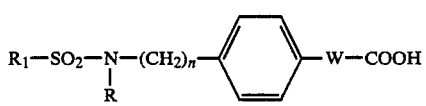

wherein R is a hydrogen atom or a lower alkyl radical;
$R_1$ is an alkyl radical or an aryl, aralkyl or aralkenyl radical, the aryl moiety of which in each case can be optionally substituted one or more times by hydroxyl, halogen, trifluoromethyl, lower alkyl or alkoxy or by acyl, carboxy or alkoxycarbonyl;
n is 1, 2 or 3; and
W is a bond or an unbranched or branched divalent aliphatic hydrocarbon chain, which is either saturated or contains a double bond, as well as the physiologically acceptable salts, esters and amides thereof.

U.S. Pat. No. 4,752,616 discloses alkylthioalkylphenyl carboxylic acids which are thromboxane receptor antagonists of the structure

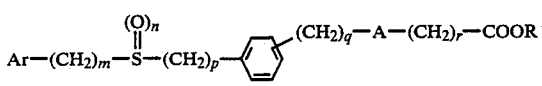

wherein Ar represents aryl which is unsubstituted or optionally substituted with one, two or three of the following: halogen, lower alkyl, lower alkoxy, phenyl, hydroxy, alkanoyl, aroyl, alkylamino, alkoxycarbonyl or carboxy;

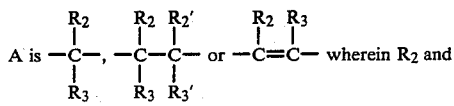

$R_3$, and $R_2'$ and $R_3'$ may be the same or different and are independently selected from hydrogen or lower alkyl,
R is hydrogen, alkali metal (such as Na, K or Li) or lower alkyl,
n is 0, 1 or 2,
m is 0, 1, 2 or 3,
p is 1 to 5,
q is 0, 1, 2 or 3, and
r is 0, 1, 2 or 3.

The $(CH_2)_m$, $(CH_2)_p$, $(CH_2)_q$ and $(CH_2)_r$ groups may be optionally substituted with one or two lower alkyl and/or one or two lower alkoxy substituents.

The $-(CH_2)_q-A-(CH_2)_r-COOR$ group may be attached at the ortho, meta or para position, with para being preferred.

European Patent Application No. 0,056,172 A2 discloses phenoxy- and thiophenoxy compounds, methods for their preparation and pharmaceutical formulations containing them having the formula I

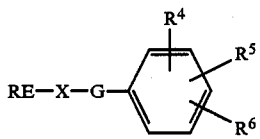

in which R is a group of formula II

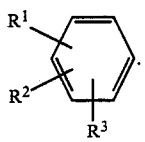

$R^1$, $R^2$ and $R^3$, which may be the same or different each represent hydrogen, alkyl, alkenyl, alkenyloxy, halogen, alkoxy, alkanoyl or hydroxy,
one or more of $R^4$, $R^5$ and $R^6$ represents alkyl, alkanoyl, alkenyl, —COOH or —ACOOH where A represents Y, OY or SY and Y represents a —CH=CH—, methylene, ethylene or 1,3-propylene chain, and the remainder of $R^4$, $R^5$ and $R^6$ represent hydrogen,
X represents a hydrocarbon chain having from 2 to 7 carbon atoms optionally substituted by hydroxy,
E represents —S—, —O—, or —CH$_2$—, and
G represents —S— or —O—, (with various exceptions)
and pharmaceutically acceptable derivatives of those compounds containing an acidic function.

These compounds are disclosed as antagonists of the slow reacting substance of anaphylaxis.

U.S. Pat. No. 4,752,613 to Floyd et al. discloses compounds of the structure

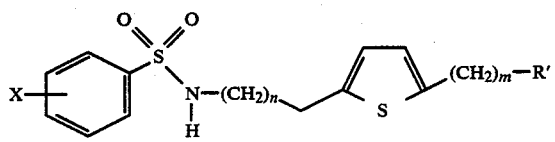

wherein X is halogen, lower alkyl, arylalkyl, alkoxy or hydroxy; wherein the phenyl ring is mono or disubstituted, R' is —COOH or

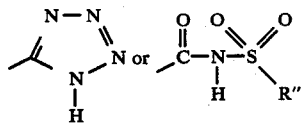

wherein R" is lower alkyl or aryl and n and m are independently zero, one, two or three which are potent thromboxane A₂ receptor antagonists.

DESCRIPTION OF THE INVENTION

In accordance with the present invention, phenylsulfone alkenoic acid compounds are provided having the following structural formula:

$$Ar-\overset{O}{\underset{O}{\overset{\|}{S}}}-(CH_2)_n-CH=CH-(CH_2)-X \qquad I$$

wherein Ar represents aryl which is unsubstituted or optionally substituted with one, two or three of the following: halogen, lower alkyl, lower alkoxy, phenyl, hydroxy, alkanoyl, aroyl, alkylamino, alkoxycarbonyl or carboxy;

X is COOR where R is hydrogen, alkali metal (such as Na, K or Li) or lower alkyl, or X is 5-tetrazolyl or

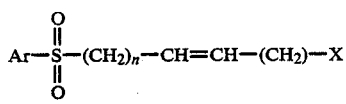

wherein
R' is lower alkyl or aryl;
n is 2, 3 or 4, and
m is 2, 3, or 4.

The $(CH_2)_m$ and $(CH_2)_n$ groups may be optionally substituted with one or two lower alkyl and/or one or two lower alkoxy substituents.

The term "lower alkyl" or "alkyl" as employed herein by itself or as part of another group includes both straight and branched chain hydrocarbon radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including one to three halo-substituents, such as F, Br, Cl or I or CF₃, an alkoxy substituent, an aryl substituent, an alkyl-aryl substituent, a haloaryl substituent, an alkyl-aryl substituent, a haloaryl substituent, a cycloalkyl substituent or an alkylcycloalkyl substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), and/or 1 or 2 lower alkoxy groups.

The term "aralkyl", "aryl-alkyl" or "aryl-lower alkyl" as used herein by itself or as part of another group refers to lower alkyl groups as discussed above having an aryl substituent, such as benzyl.

The terms "alkanoyl" and "aroyl" refer to a lower alkyl group linked to a carbonyl group or an aryl group linked to a carbonyl group.

The term "halogen" or "halo" as used herein by itself or as part of another group refers to chlorine, bromine, fluorine or iodine, with chlorine being preferred.

The terms "$(CH_2)_m$" and "$(CH_2)_n$" each independently include a straight or branched chain radical having 2 to 4 carbons in the normal chain and may contain one or more lower alkyl and/or lower alkoxy substituents. Examples of $(CH_2)_m$ and $(CH_2)_n$ groups include —CH₂CH₂—,

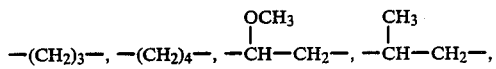

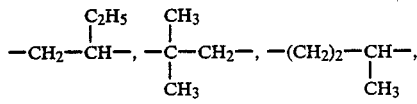

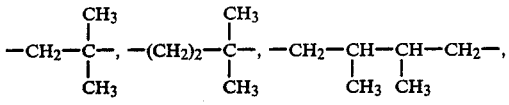

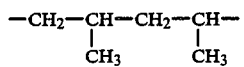

and the like.

Preferred are those compounds of the invention wherein Ar is halophenyl, such as p—Cl—C₆H₄—, $(CH_2)_n$ is is $(CH_2)_3$ or $(CH_2)_4$, $(CH_2)_m$ is $(CH_2)_2$, $(CH_2)_3$ or

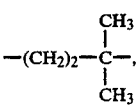

and X is COOH.

The various compounds of the invention may be prepared as outlined below.

Compounds of the invention may be prepared starting with the mercaptan A

   A which is alkylated by treating A with a strong base such as an alkali metal alkoxide like potassium t-butoxide, sodium methoxide or sodium ethoxide and alkylating agent B Br—(CH$_2$)$_n$—CN   B in the presence of an inert organic solvent like tetrahydrofuran, dimethyl sulfoxide or ethanol to form the sulfide compound II Ar—S—(CH$_2$)$_n$—CN   II The above reaction is carried out at a temperature within the range of from about 20° to about 80° C. employing a molar ratio of A:base within the range of from about 0.8:1 to about 3:1 and preferably from about 1:1 to about 1.5:1, and a molar ratio of B:A of within the range of from about 0.8:1 to about 1.2:1 and preferably from about 0.9:1 to about 1.1:1.

Nitrile II is dissolved in an inert organic solvent such as tetrahydrofuran (THF) and is then reduced by treatment with diisobutylaluminum hydride in the presence of an inert organic solvent, such as toluene, benzene or tetrahydrofuran under an inert atmosphere, such as argon, at a temperature within the range of from about −20° C. to about 0° C. to form aldehyde III Ar—S—(CH$_2$)$_n$—CHO.   III Aldehyde III is then subjected to a Wittig reaction wherein the ylide, prepared from a mixture of phosphonium bromide C

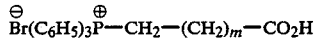

in inert organic solvent such as dry tetrahydrofuran under an inert atmosphere such as argon treated with a strong base such as potassium t-amylate or potassium t-butoxide, is reacted with aldehyde III in inert organic solvent such as dry tetrahydrofuran, to form the thio acid IV Ar—S—(CH$_2$)$_n$—CH=CH—(CH$_2$)$_m$—CO$_2$H.   IV Sulfide IV may converted to the corresponding sulfone by oxidizing sulfide IV employing an oxidizing agent, such as Oxone ® (Dupont, 2KHSO$_5$ 5 . KHSO$_4$ . K$_2$SO$_4$) employing a molar ratio of oxidizing agent:IV of within the range of from about 2:1 to about 6:1 and preferably from about 3:1 to about 5:1 to form sulfone IA

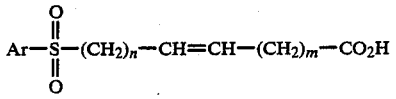   IA which may be purified by treatment with a diazoalkane esterifying agent such as diazomethane in the presence of an inert solvent such as ethyl ether, to form the ester of the invention IB

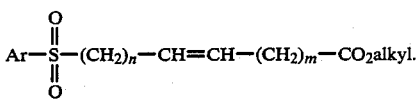   IB

The ester IB may be converted to acid compound IA of the invention by subjecting IB to basic hydrolysis by treatment with a base such as lithium hydroxide, sodium hydroxide or potassium hydroxide to form the corresponding alkali metal salt, followed by neutralization with an acid such as dilute hydrochloric acid or oxalic acid to form IA.

In an alternative method, compounds of the invention wherein n is 2 or 3 may be prepared as follows.

Mercaptan A is alkylated by treating A with a strong base such as an alkali metal hydroxide like potassium t-butoxide, sodium methoxide or sodium ethoxide and an alkylating agent, namely, protected bromoalkenyloxy compound of the structure D Br—(CH$_2$)$_n$—CH=CH—(CH$_2$)$_m$—OPro   D wherein Pro represents an alcohol protecting group such as

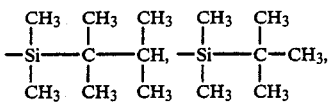

or

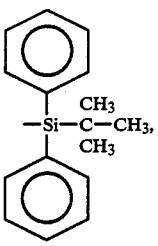

in the presence of an inert organic solvent like tetrahydrofuran, dimethyl sulfoxide or ethanol to form the sulfide compound IV which may be oxidized to the sulfone I as described hereinbefore.

The above reaction is carried out at a temperature within the range of from about 20° to about 80° C. employing a molar ratio of A:base within the range of from about 0.8:1 to about 3:1 and preferably from about 1:1 to about 1.5:1, and a molar ratio of D:A of within the range of from about 0.8:1 to about 1.2:1 and preferably from about 0.9:1 to about 1.1:1.

Where it is desired to include an alkyl group in the $(CH_2)_m$ group (at position 2), conventional procedures may be employed using the sulfide alkyl ester H as the starting material

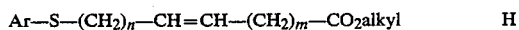

(which is prepared by treating the acid IV with a diazoalkane).

Compounds of the invention where R is 5-tetrazolyl, that is,

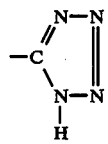

may be prepared starting with ester IB which is treated with a saturated alcoholic solution of ammonia to form the corresponding amide V

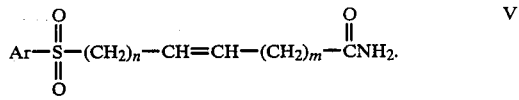

The amide V is then dehydrated by treating V with a sulfonyl chloride and pyridine to form the corresponding nitrile VI

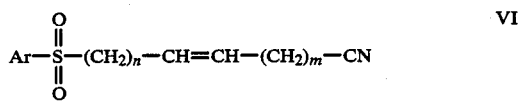

which is subjected to a cycloaddition reaction by treating VI with an inorganic azide such as $NaN_3$, and ammonium chloride employing a molar ratio of VI:azide of within the range of from about 0.7:1 to about 1:1 to form the tetrazole IC

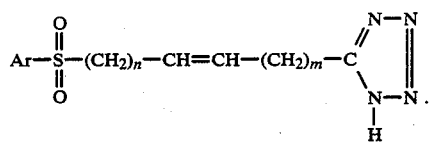

Compounds of the invention wherein X is

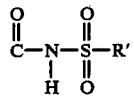

may be prepared by treating acid of the invention IA with a coupling reagent such as carbonyldiimidazole (CDI) or 3-(3-dimethylaminopropyl)ethyl carbodiimide and an alkyl or arylsulfonamide and an amine such as 4-dimethylaminopyridine in the presence of an inert solvent such as THF or dimethylformamide, at a temperature within the range of from about 10° to about 50°

C. employing a molar ratio of IA:CDI of within the range of from about 0.9:1 to about 1.1:1 and a molar ratio of IA:sulfonamide of within the range of from about 1:1 to about 0.5:1 to form the sulfonamide ID of the invention

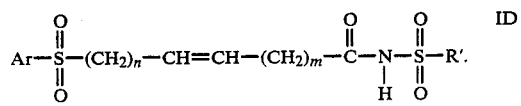

The starting material D may be prepared by starting with protected acetylenic compound E

wherein Pro is a protecting group as defined hereinbefore prepared by silylation of an acetylene compound of the structure F

Acetylene compound E in inert organic solvent such as tetrahydrofuran (THF) or ethyl ether, under an inert atmosphere such as argon, is treated with a lithiated strong base such as an alkyl lithium compound like n-butyl lithium, lithium diisopropylamide or lithium bistrimethylsilylamide in an inert organic solvent such as hexane, ethyl ether or THF while cooling the resulting solution to from about −80° C. to about −50° C. and reacting same with ethylene oxide or trimethylene oxide and boron trifluoride in ethyl ether under reduced temperature of from about −80° C. to about −60° C. to form the alcohol G

A solution of the alcohol G in inert solvent such as toluene under an inert atmosphere such as argon is then reduced by treating with Lindlar catalyst and hydrogen to form the olefin H

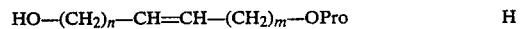

Olefin H is then brominated by treatment with a slurry of triphenylphosphine dibromide in an inert solvent such as toluene under an inert atmosphere such as argon to form starting material D.

The compounds of this invention are cardiovascular agents useful as platelet aggregation inhibitors, e.g., for treatment of thrombotic disease, such as coronary or cerebral thromboses. In addition, the compounds of the invention are useful in inhibiting bronchoconstriction such as associated with asthma and airways hyperactivity. They are also selective thromboxane $A_2$ receptor antagonists, e.g., having a vasodilatory effect for treatment of myocardial ischemic disease, such as angina pectoris.

In addition, the compounds of the invention may be useful in improving post-ischemic myocardial dysfunction, for example, decreased contractile dysfunction, decrease in tissue necrosis, and decrease in infarct size, preventing or treating toxemia in pregnancy, preventing or reducing platelet loss during extracorporeal circulation, potentiating diuretic-induced diuresis, preventing or reducing adverse reactions to protamine, preventing thrombosis and adverse reactions to radiographic contrast agents, preventing or reducing venous thrombosis (in conjunction with heparin), treating burn injury and promoting wound healing, treating ischemia (alone or in combination with a calcium channel blocker), preserving vascular patency and circulation during and following vascular surgery, preventing reperfusion injury after CNS ischemic states like stroke or vascular surgery, treating tardive dyskenesia, treating Raynaud's disease, treating unstable angina, treating purpura fulminarus, and treating thrombotic thrombocytopenia purpura. Furthermore, the compounds of the invention may be useful in the treatment of pulmonary embolism, diabetic retinopathy, and in coronary artery by-pass, renal dialysis, thrombolysis, endarterectomy, acute renal failure, peripheral vascular disease, intermittent claudication, pulmonary hypertension after mitral valve surgery, pulmonary hypertension after intralipid infusion, subarachnoid hemorrhage, treating or preventing complications following organ transplant (particularly cardiac or renal), treating persistent pulmonary hypertension of the newborn, treating tuberculosis and enhancing immune surveillance and promoting antibiotic penetration to sites of infection/abscess.

The compounds of the invention can be administered orally or parenterally to various mammalian species known to be subject to such maladies, e.g., humans, cats, dogs and the like in an effective amount within the dosage range of about 1 to 100 mg/kg, preferably about 1 to 50 mg/kg and especially about 2 to 25 mg/kg (or from about 5 to about 2500 mg, preferably from about 10 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I or in topical form for wound healing (0.01 to 5% by weight compound of formula I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

Example 1

9(4-Chlorophenyl)sulfonyl]-5-nonenoic acid

A. 5-[(4-Chlorophenyl)sulfonyl]valeronitrile

To a stirred solution of potassium t-butoxide (4.01 g, 35.75 mmol) and 4-chlorothiophenol (5.17 g, 35.8 mmol) in dry tetrahydrofuran (80 mL) was added 5-bromovaleronitrile (3.48 mL, 29.8 mmol) dropwise over 5 minutes.

After stirring overnight the resulting mixture was diluted with 400 ml of ethyl ether and washed with 0.2N aqueous NaOH solution (3×60 ml) and saturated NaHCOa solution (1×100 ml), dried (MgSO$_4$), filtered and concentrated in vacuo. Chromatography of 120 g of Merck silica gel 60 using 4:1 hexane-ether as eluant gave 6.11 g (91%) of title nitrile. TLC: silica gel, 4:1 hexane-ether, R$_f$=0.20, Ce(SO$_4$)$_2$.

B. 5-[(4-Chorophenyl)sulfonyl]pentanal

To a stirred solution of Part A nitrile (3.0 g, 13.3 mmol) in 100 mL of dry THF under argon at −20° C. was added dropwise a solution of 1.5M diisobutyl aluminum hydride (DIBAL) in toluene (26.6 mL, 39.9 mmol) over 20 minutes. The reaction mixture was stirred at 0° C. for 2 hours and quenched by the dropwise addition of 200 mL of acetone. To this mixture was added sequentially 40 g of Baker silica gel (200 mesh), 1 mL of H$_2$O and 1 mL of acetic acid. The solid was filtered off and rinsed with acetone (4×100 mL). The filtrate was concentrated in vacuo. The residue was purified by a filter column (3" pad of Merck silica gel 60) using 1:1 hexane-ether as eluant to give pure title aldehyde (2.53 g, 83%). TLC: silica gel, 4:1, hexane-ether, R$_f$0.25, Ce(SO$_4$)$_2$.

C. 9-[(4-Chlorophenyl)thio]-5(Z)-nonenoic acid

To a stirred mixture of phosphonium bromide

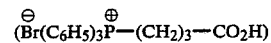

in dry THF (120 mL) at 0° C. under argon was added dropwise over 15 minutes 1.6M K-t-amylate (18.69 mL, 29.89 mmol). After 1 hour, a yellow colored milky suspension was observed. Twelve milliliters of dimethyl sulfoxide was added and the mixture stirred vigorously. After stirring for 3 hours, the mixture was yellow-brown in color. A solution of Part B aldehyde (2.53 g, 11.7 mmol), in dry THF (60 mL) was added over 50 minutes and the mixture was stirred overnight at room temperature.

The mixture was cooled at 0° C., quenched with 5 ml of acetic acid and concentrated in vacuo, partitioned between 100 mL of 0.1N HCl solution and hexane:ethyl ether 1:1 (4×120 mL), dried (MgSO$_4$), filtered and concentrated in vacuo to give 6.5 g crude title compound. Purification was effected by flash chromatography on 120 g of Merck silica gel 60 using 2:1 hexane-ether as eluant to give 2.13 g (64%) of title acid. TLC: silica gel, 1:2 hexane-ether, R$_f$=0.68, Ce(SO$_4$)$_2$.

D. 9-[(4-Chlorophenyl)sulfonyl]-5(Z)-nonenoic acid, methyl ester

Part C thio acid (1 g), methanol (50 mL), THF (50 mL) and a solution of 5 g of Oxone® in 50 mL H₂O were combined and the mixture stirred vigorously at room temperature overnight and then was extracted with ethyl acetate (4×70 mL), dried (MgSO₄), filtered and concentrated in vacuo. The concentrate was chromatographed on 60 g of Merck silica gel 60 using 2% methanol/methylene chloride as eluent to give 890 mg of a 1:1 mixture of sulfone acid and the lactone

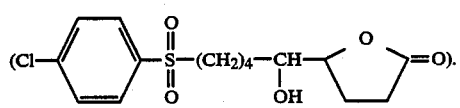

The mixture was diluted with 100 mL of 0.1N NaOH solution and extracted with ethyl ether (3×150 mL). The aqueous layer was acidified to pH 2 by 1N HCl (aqueous) and extracted with ethyl acetate (3×180 mL), dried (MgSO₄), filtered and concentrated in vacuo to give crude sulfone acid (580 mg) which still contained some lactone. The crude sulfone acid was diluted with 50 mL of ethyl ether at room temperature and the solid (150 mg) lactone was filtered off. The filtrate was concentrated in vacuo, dissolved in 30 mL of ethyl ether and stored in the freezer. The resulting precipitate was removed by filtration and the filtrate was concentrated to give 360 mg of crude sulfone acid which still contained some lactone.

A solution of this mixture (360 mg) in 50 mL of ether was treated with ethereal CH₂N₂ at room temperature for 1.5 hours and the excess CH₂N₂ was destroyed by the addition of acetic acid. Purification was effected by flash chromatography on 44 g of Merck silica gel using 4:1 hexane-ether as eluant to give 260 mg (26%) of title methyl ester. TLC: silica gel, 1:1 hexane-ether, $R_f$=0.68, Ce(SO₄)₂.

E. 9-[(4-Chlorophenyl)sulfonyl]-5(Z)-nonenoic acid

To a stirred solution of Part D methyl ester (260 mg, 0.76 mmol) in 50 mL of freshly distilled THF and 8 mL of H₂O was added 8 mL of 1N aqueous LiOH solution. The mixture was stirred at room temperature for 15 hours and acidified to pH 2 by the addition of 1N N aqueous HCl solution. This mixture was saturated with NaCl and the THF layer was separated. The aqueous layer was extracted with ethyl acetate (3×60 mL). The combined organic extracts was dried (MgSO₄), filtered and concentrated in vacuo. Purification was effected by flash chromatography on 24 g of Merck silica gel 60 using 3% CH₃OH in CH₂Cl₂ as eluant to give 220 mg (88%) of pure title acid. TLC: silica gel, 6% CH₃OH in CH₂Cl₂, $R_f$=0.42, Ce(SO₄)₂, m.p. 62°-64° C. ¹³C NMR (67.5 MHz, CDCl₃): δ 178.8, 140.4, 137.6, 130.1, 129.6, 129.6, 129.6, 128.2, 56.2, 33.9, 28.0, 26.5, 22.5, 22.2.

EXAMPLE 2

9-[(4-Chlorophenyl)sulfonyl]-4(Z)-nonenoic acid

A. Dimethyl(9-hydroxy-non-5-yn-1-oxy)-(1,1,2-trimethylpropyl)silane

To a stirred solution of the acetylene (36.6 g, 153 mmol, prepared by silylation of 5-hexyn-1-ol with dimethylthexylsilylchloride, in 300 mL of dry tetrahydrofuran (THF) under argon at −78° C. was added dropwise a 2.5 M solution of n-butyl lithium in hexane (64 mL, 160 mmol) over 10 minutes. The pot temperature was kept below −70° C. during this addition. The mixture was stirred at −78° C. for 30 minutes at which time trimethylene oxide (11.9 mL, 183 mmol) was added followed immediately by BF₃ ethyl ether (19.7 mL, 160 mmol) at a rate such that the pot temperature did not exceed −60° C. The addition on this scale required 15 minutes. The reaction mixture was stirred at −78° C. for 10 minutes and then quenched by the addition of 153 mL of saturated NaHCO₃ solution. The mixture was warmed to room temperature and concentrated in vacuo. The residue was partitioned between 300 mL of saturated NaHCO₃ solution and ethyl ether (×400 mL). The combined ether extracts was dried (MgSO₄), filtered and concentrated in vacuo. The crude alcohol was subjected to bulb to bulb distillation between 160° C. and 220° C. under vacuum to give 14.8 g of pure title alcohol. The undistilled residue was chromatographed on 150 g of Merck silica gel with gradient elution of hexane-ether to give an additional 12.1 g of pure title alcohol. The total yield was 59%. TLC: silica gel, 1% CH₃OH in CH₂Cl₂, $R_f$=0.40, Ce(SO₄)₂.

B. Dimethyl(9-hydroxynon-5(Z)-en-1-oxy) (1,1,2-trimethylpropyl)silane

To a stirred solution of Part A alcohol (24.8 g, 83.2 mmol) in 200 mL of toluene under argon was added Lindlar catalyst (1.24 g, 5% by weight of Part A alcohol). The atmosphere was exchanged for hydrogen by several vacuum-fill cycles. This mixture was stirred at room temperature for 2.5 hours and the catalyst was removed by filtration through a 3″ pad of Celite. The total hydrogen uptake was 2.3 L. The filtrate was concentrated in vacuo to give 24.4 g (8%) of title olefin which was used for the next transformation without any further purification. TLC: silica gel, 1% CH₃OH in CH₂Cl₂, $R_f$=0.40, CE(SO₄)₂.

C. Dimethyl(9-bromonon-5(Z)-en-1-oxy) (1,1,2-trimethylpropyl)silane

To a stirred solution of triphenylphosphine (4.37 g, 16.7 mmol) in 100 mL of toluene at 0° C. under argon was added dropwise bromine (0.85 mL, 16.7 mmol) over 10 minutes. This mixture was stirred at 0° C. for 80 minutes at which time a solution of Part B olefin (5.0 g, 16.7 mmol) and pyridine (1.35 mL, 16.7 mmol) in 25 mL of toluene was added dropwise over 20 minutes. The reaction mixture was stirred at 0° C. for 1 hour and at room temperature for 2 hours. This mixture was diluted with 600 mL of ethyl ether and the precipitate was removed by filtration. The filtrate was washed with 1N aqueous HCl solution (2×70 mL), saturated NaHCO$_3$ solution (1×70 mL) and brine (1×100 mL). The organic layer was dried (MgSO$_4$), filtered and concentrated in vacuo. This was chromatographed on 120 g of Merck silica gel 60 using 2% ethyl acetate/hexane as eluant to give 5.5 g (91%) of title bromide. TLC: silica gel, hexane-benzene 4:1, R$_f$=0.86, Ce(SO$_4$)$_2$.

D.
Dimethyl[9-[(4-chlorophenyl)thio]-non-4-(Z)-en-1-oxy](1,1,2-trimethyl)silane To a stirred solution of potassium t-butoxide (1.62 g, 14.5 mmol) in tetrahydrofuran (20 mL) was added 4-chlorobenzene mercaptan (2.09 g, 14.5 mmol). Then a solution of Part C bromide (3.5 g, 9.64 mmol) in tetrahydrofuran (15 mL) was added. The mixture was stirred at room temperature for 4 hours and then partitioned between 200 mL of ethyl ether and 30 mL of 0.2N NaOH solution. The ether layer was washed with 0.2N NaOH (30 mL), saturated NaHCO$_3$ solution (30 mL), dried (MgSO$_4$), filtered and concentrated in vacuo to give title compound.

E. 9-[(4-Chlorophenyl)sulfonyl]-4(Z)-nonenoic acid

To a stirred solution of part D sulfide (9.64 mmol maximum) in 120 mL each of CH$_3$OH and THF was added a solution of 4.96 g Oxone ® in 120 mL of H$_2$O. This mixture was stirred vigorously for 17 hours and then concentrated in vacuo. The residue was diluted with 20 mL of H$_2$O and extracted with ethyl acetate (5×80 mL). The combined organic layers were dried (MgSO$_4$), filtered, and concentrated in vacuo. The crude sulfone was immediately oxidized as follows. The sulfone was dissolved in 50 mL acetone, cooled to 0° C. and treated with approximately 4 mL of Jones reagent. This was stirred for 50 minutes and then the reaction was quenched by the addition of isopropyl alcohol. The reaction mixture was partitioned between 40 mL of H$_2$O and ethyl acetate (2×15 mL). Combined organics was dried (MgSO$_4$), filtered and concentrated in vacuo to afford crude title acid.

Purification was effected by flash chromatography on 70 g of Merck silica gel 60 using 0.2 L each of 1%, 2%, 4%, 6% and 10% CH$_2$OH in CH$_2$Cl$_2$ as eluant to give 1.0 g of a mixture of desired title sulfone acid and some fast moving impurity. This mixture was chromatographed on 40 g of Merck silica gel 60 using 0.3 L each of 1% and 2% CH$_2$OH in CH$_2$Cl$_2$ as eluant to give (90 mg, 16%) of pure title sulfone acid and 800 mg impure title sulfone acid. TLC: silica gel, 6% CH$_3$OH in CH$_2$Cl$_2$, R$_f$=0.52, Ce(SO$_4$)$_2$. $^{13}$C NMR (67.5 MHz, CDCl$_2$): δ 179.3, 140.4, 137.5, 130.6, 129.6, 129.6, 128.2, 55.6, 33.2, 26.4, 25.5, 24.3, 22.5.

EXAMPLE 3
9-[(4-Chlorophenyl)sulfonyl]-4(Z)-(2,2-dimethyl)-nonenoic acid, methyl ester

A. 9-[(4-Chlorphenyl)thio]-4(Z)-nonenoic acid, methyl ester

To a stirred solution of Example 2, Part C silyl ether (1.67 g, 4.60 mmol) in 100 mL of acetone at 0° C. was added Jones reagent (CrO$_3$, H$^+$) until an orange red color persisted. This mixture was stirred at 0° C. for 20 minutes and at room temperature for 25 minutes. The mixture was quenched with isopropyl alcohol and concentrated in vacuo. The residue was partitioned between 200 mL of H$_2$O and ethyl ether (4×200 mL). The combined ether extracts was dried (MgSO$_4$), filtered and concentraed in vacuo. This acid was then treated with ethereal CH$_2$N$_2$ in CH$_3$OH at room temperature to give bromide ester. This crude bromide ester was coupled with 4-chlorothiophenol as follows:

To a stirred solution of 4-chlorothiophenyl (2.2 g), dry tetrahydrofuran (15 ml) and potassium t-butoxide (1.62 g) under argon was added a solution of the above-prepared bromide ester in dry tetrahydrofuran (15 ml) over 5 minutes.

The resulting mixture was stirred for 5.6 hours, diluted with 300 ml of ethyl ether and washed with 0.2N NaOH solution (3×40 ml), saturated NaHCO$_3$ solution (1×40 ml), dried (MgSO$_4$), filtered and concentrated in vacuo to give title compound. Purification was effected by flash chromatography on 45 g of Merck silica gel 60 using 3% ethyl acetate in hexane to give 1.08 g (75%) of title sulfide as an oil. TLC: silica gel, 5% ethyl acetate in hexane, R$_f$=0.48, Ce(SO$_4$)$_2$.

B. 9-[(4-Chlorophenyl)thio]-4(Z)-(2-methyl)nonenoic acid, methyl ester

To a stirred solution of dry diisopropyl amine (0.24 mL, 1.68 mmol) in 5 mL of dry tetrahydrofuran (THF) under argon at −78° C. was added dropwise a solution of 2.5M n-butyl lithium hexane (0.65 mL, 1.62 mmol) over 2 minutes. This mixture was stirred at −78° C. for 40 minutes and at 0° C. for 15 minutes. To this mixture at −78° C. under argon was added a solution of Part A sulfide (420 mg, 1.35 mmol) in 5 mL of dry THF over 10 minutes. This mixture was stirred at −78° C. for 30 minutes at which time a solution of dry hexamethylphosphorictriamide (0.28 mL, 1.62 mmol) and CH$_3$I (0.17 mL, 2.69 mmol, filtered through a pad of basic Alumina prior to use) in 5 mL of dry THF over 5 minutes. The reaction mixture was stirred at −78° C. for 2 hours and was quenched by the dropwise addition of a solution of 1 mL of acetic acid in 4 mL of THF. The resulting mixture was partitioned between 50 mL of saturated NaHCOs solution and ethyl ether (4×70 mL). The combined ether extracts was dried (MgSO$_4$), filtered and concentrated in vacuo. This was chromatographed on 44 g of Merck silica gel 60 using 3% ethyl acetate in hexane as eluant to give 390 mg of title monomethylated ester as an oil. TLC: silica gel, hexane-ether 4:1, R$_f$=0.86, Ce(SO$_4$)$_2$.

C. 9-[(4-Chlorophenyl)thio]-4(Z)-(2,2-dimethyl)-nonenoic acid, methyl ester

Part B monomethylated ester (630 mg, 1.93 mmol) was alkylated with CH$_z$I as described in Part B. Purification was effected by flash chromatography on 48 g of Merck silica gel 60 using 3% ethyl acetate in hexane as eluant to give 410 mg (62%) of title dimethylated ester. TLC: silica gel, hexane-ether 4:1, R$_f$=0.90, I$_2$.

Example 4

9-[(4-Chlorophenyl)sulfonyl]-4(Z)-(2,2-dimethyl)-nonenoic acid

To a solution of 490 mg (1.44 mmol) of Example 3 title ester in 50 mL each of THF and CH$_2$OH was added a solution of 4 g of Oxone® in 50 mL of water. This mixture was stirred for 13.5 hours at room temperature and then concentrated in vacuo. The residue was partitioned between 30 mL of H$_2$O and 120 mL ethyl acetate. The aqueous layer was extracted with ethyl acetate (3×120 mL). Combined organic extracts was dried (MgSO$_4$), filtered and concentrated in vacuo to give 400 mg (75%) of the sulfone ester. To a stirred solution of the sulfone in 2 mL of CH$_3$OH was added 10 mL of 2N N̲ aqueous KOH solution. This mixture was heated at 50° C. for 2 hours and refluxed for 4 hours. The cooled reaction mixture was acidified to pH 2 by the addition of 2N N̲ aqueous HCl solution and extracted with ethyl acetate (4×50 mL). The combined ethyl acetate extracts was dried (MgSO$_4$), filtered and concentrated in vacuo. This was chromatographed on 40 g of Merck silica gel 60 using 0.2 L each of 2% and 4% CH$_3$OH as eluant to give 290 mg (75%) of pure title acid as an oil. TLC: silica gel, 4% CH$_3$OH in CH$_2$Cl$_2$, R$_f$=0.45, Ce(SO$_4$)$_2$. $^{13}$C NMR (67.5 MHz, CDCl$_3$): δ 183.9, 140.3, 137.6, 131.3, 129.5, 129.5, 129.5, 129.5, 127.4, 55.6, 42.0, 40.1, 25.5, 24.9, 24.9, 22.9, 22.5.

EXAMPLES 5 TO 16

Following the procedures of Example 1 except substituting for Example 1 part A bromide the bromoalkyl nitrile compound shown in Column II of Table I set out below, substituting for 4-chlorobenzenemercaptan, the sulfide shown in Column I, and substituting for the phosphonium bromide, the bromide shown in Column III, the product shown in Column IV is obtained.

It will be appreciated that wherein the Ar group in the starting materials shown in Column I includes substituents that include acidic hydrogens such as OH or primary or secondary amine then these starting materials will be reacted with a protecting compound such as set out hereinbefore with respect to "Pro" and the Pro group will be removed as a final step as described above.

| Ex. No. | Column I<br>ArSH<br>Ar | Column II<br>Br—(CH$_2$)$_n$—CN<br>(CH$_2$)$_n$ | Column III<br>$\overset{\oplus}{\text{Br}}$(C$_6$H$_5$)$_3$P—(CH$_2$)$_m$—CO$_2$H<br>(CH$_2$)$_m$ | Column III<br>Ar—S(=O)(=O)—(CH$_2$)$_n$—CH=CH—(CH$_2$)$_m$—COOH<br>Ar / (CH$_2$)$_n$ / (CH$_2$)$_m$ |
|---|---|---|---|---|
| 5 | phenyl | —CH$_3$—CH(CH$_3$)— | —(CH$_2$)$_3$— | Same as Col. I, II and III |
| 6 | naphthyl | —CH$_2$—CH$_2$— | —(CH$_2$)$_3$— | |
| 7 | 4-fluorophenyl | —CH$_2$—C(H)(CH$_3$)—CH(CH$_3$)— | —(CH$_2$)$_4$— | |
| 8 | 3-hydroxyphenyl | —CH(C$_2$H$_5$)—CH$_2$— | —CH$_2$—CH(CH$_3$)—CH$_2$— | |
| 9 | 3-methoxyphenyl | —CH$_2$—CH$_2$—CH(CH$_3$)—CH$_2$— | —CH$_2$—CH(CH$_3$)—CH$_2$— | |
| 10 | 6-methylnaphthyl | —CH(CH$_3$)—CH(CH$_3$)— | —(CH$_2$)$_3$— | Same as Col. I, II and III |
| 11 | biphenyl | —CH(CH$_3$)—CH$_2$— | —(CH$_2$)$_4$— | |

-continued

| Ex. No. | Column I<br>ArSH<br>Ar | Column II<br>Br—(CH$_2$)$_n$—CN<br>(CH$_2$)$_n$ | Column III<br>$\overset{\oplus}{\text{Br}}$(C$_6$H$_5$)$_3$P—(CH$_2$)$_m$—CO$_2$H<br>(CH$_2$)$_m$ | Column III<br>Ar—S(O)(O)—(CH$_2$)$_n$—CH=CH—(CH$_2$)$_m$—COOH<br>Ar    (CH$_2$)$_n$    (CH$_2$)$_m$ |
|---|---|---|---|---|
| 12 | 4-C$_4$H$_9$—C$_6$H$_4$— | —(CH$_2$)$_3$— | —CH$_2$—CH$_2$—CH$_2$— | |
| 13 | 4-CH$_3$O—biphenyl— | —CH$_2$—CH(CH$_3$)—CH(CH$_3$)— | —CH(CH$_3$)—(CH$_2$)$_2$— | |
| 14 | 4-(CH$_3$—NH)—C$_6$H$_4$— | —(CH$_2$)$_4$— | —(CH$_2$)$_3$— | |
| 15 | 4-Br—C$_6$H$_4$— | —CH$_2$—CH$_2$— | —(CH$_2$)$_3$— | Same as Col. I |
| 16 | 4-Br—C$_6$H$_4$— | —CH$_2$—CH$_2$— | —(CH$_2$)$_4$— | Same as Col. II and III |

EXAMPLES 17 TO 28

Following the procedure of Examples 2 to 4 except substituting for the acetylene silyl compound, the acetylene silyl compound shown in Column I of Table II, substituting for trimethylene oxide, the oxide shown in Column II, and substituting for p-chlorobenzenemercaptan, the compound shown in Column III, the product shown in Column IV is obtained.

What is claimed is:

1. A compound having the structure $$Ar-\overset{O}{\underset{O}{\overset{\|}{S}}}-(CH_2)_n-CH=CH-(CH_2)_m-X$$

TABLE II

| Ex. No. | Column I<br>C≡C—(CH₂)ₘ—OPro*<br>  |<br>H<br>(CH₂)ₘ | Column II<br>(CH₂)ₙ\O/<br>(CH₂)ₙ | Column III<br>Ar—SH<br>Ar | Column IV<br>Ar—S(O)₂—(CH₂)ₙ—CH=CH—(CH₂)ₘ—COOH<br>(CH₂)ₙ    (CH₂)ₘ    Ar |
|---|---|---|---|---|
| 17 | —(CH₂)₃— | —CH₃—CH(CH₃)— | phenyl | Same as Col. II   Same as Col. I   Same as Col. III |
| 18 | —CH₂CH₂— | —CH₂—CH₂— | naphthyl | |
| 19 | —(CH₂)₄— | —(CH₂)₃— | F-phenyl | |
| 20 | —(CH₂)₃— | —CH—CH(CH₃)— | HO-phenyl (m-) | |

| Ex. No. | Column I<br>HC≡C—(CH₂)ₘ—OPro<br>(CH₂)ₘ | Column II<br>(CH₂)ₙ\O/<br>(CH₂)ₙ | Column III<br>Ar—SH<br>Ar |
|---|---|---|---|
| 21 | —CH(CH₃)—CH₂CH₂— | —CH₂—CH₂— | CH₃O-phenyl |
| 22 | —CH(CH₃)—CH₂— | —CH₂—CH₂— | CH₃-naphthyl |
| 23 | —CH₂—CH₂—CH₂— | —CH₂—CH—₂— | biphenyl |
| 24 | —CH₂CH₂CH₂— | —(CH₂)₃— | CH₃—C(O)-phenyl |
| 25 | —(CH₂)₃— | —CH₂—CH₂—CH(CH₃)— | F-phenyl |
| 26 | —CH(CH₃)—CH₂— | —CH₂CH₂— | Br-phenyl |
| 27 | —CH₂CH₂— | —CH₂CH₂— | CH₃C(O)-phenyl |
| 28 | —CH(C₂H₅)—CH₂— | —CH₂CH₂— | HOOC-phenyl |

*Pro = 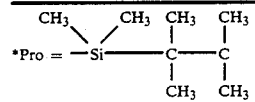

wherein Ar is a phenyl or naphthyl group which is unsubstituted or substituted with one, two or three of halogen, lower alkyl, lower alkoxy, phenyl, hydroxy, alkanoyl, benzoyl, alkylamino, alkoxycarbonyl or carboxy;

X is COOR where R is hydrogen, alkali metal or lower alkyl or X is 5 tetrazolyl or

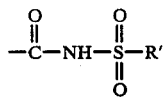

wherein
R' is lower alkyl, phenyl or naphthyl;
n is 2, 3 or 4; and
m is 2, 3 or 4;
and each of the $(CH_2)_n$ and $(CH_2)_m$ groups may be unsubstituted or optionally substituted with one or two lower alkyl groups and/or are one or two lower alkoxy groups.

2. The compound as defined in claim 1 wherein X is COOR and R is H.

3. The compound as defined in claim 1 wherein X is 5-tetrazolyl.

4. The compound as defined in claim 1 wherein X is

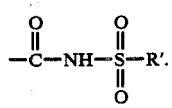

5. The compound as defined in claim 1 wherein $(CH_2)_n$ is $(CH_2)_3$ or $(CH_2)_4$ and $(CH_2)_m$ is

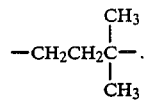

6. The compound as defined in claim 1 having the name 9-[(4-chlorophenyl)sulfonyl]-5(Z)-nonenoic acid or its methyl ester.

7. The compound as defined in claim 1 having the name methyl 9-[(4-chlorophenyl)-sulfonyl]-4-(Z)-nonenoic acid.

8. The compound as defined in claim 1 having the name methyl 9-[(4-chlorophenyl)-sulfonyl]-4(Z)-(2,2-dimethyl)nonenoic acid or its methyl ester.

9. A composition for inhibiting arachiodonic acid-induced platelet aggregation and bronchoconstriction comprising a therapeutically effective amount of a compound as defined in claim 1 and a pharmaceutically acceptable carrier therefor.

* * * * *

UNITED STATES PATENT AND TRADEMARK OFFICE
CERTIFICATE OF CORRECTION

PATENT NO. : 4,959,383
DATED : September 25, 1990
INVENTOR(S) : Steven E. Hall

It is certified that error appears in the above-identified patent and that said Letters Patent is hereby corrected as shown below:

Column 24, line 9:

Claim 5, line 3, before the formula, add

--$(CH_2)_2$, $(CH_2)_3$ or--.

Signed and Sealed this

Third Day of March, 1992

Attest:

HARRY F. MANBECK, JR.

Attesting Officer

Commissioner of Patents and Trademarks